US011341640B2

(12) United States Patent
Enzmann et al.

(10) Patent No.: US 11,341,640 B2
(45) Date of Patent: May 24, 2022

(54) APPARATUS AND METHOD FOR DETERMINING THE SPATIAL PROBABILITY OF CANCER WITHIN THE PROSTATE

(71) Applicant: THE REGENTS OF THE UNIVERSITY OF CALIFORNIA, Oakland, CA (US)

(72) Inventors: Dieter Enzmann, Beverly Hills, CA (US); Matthew S. Brown, Marina del Rey, CA (US); Corey W. Arnold, Los Angeles, CA (US); Mahesh B. Nagarajan, Sherman Oaks, CA (US); Hyun J. Kim, Porter Ranch, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 86 days.

(21) Appl. No.: 16/828,319

(22) Filed: Mar. 24, 2020

(65) Prior Publication Data
US 2020/0286232 A1    Sep. 10, 2020

Related U.S. Application Data

(63) Continuation of application No. PCT/US2018/053898, filed on Oct. 2, 2018.
(Continued)

(51) Int. Cl.
*G06T 7/00* (2017.01)
*G06T 7/143* (2017.01)
(Continued)

(52) U.S. Cl.
CPC ............ *G06T 7/0012* (2013.01); *A61B 5/004* (2013.01); *A61B 5/055* (2013.01); *A61B 5/4381* (2013.01);
(Continued)

(58) Field of Classification Search
CPC ....... G06T 7/0012; G06T 7/143; G06T 7/337; G06T 11/0065; G06T 2207/10088;
(Continued)

(56) References Cited

U.S. PATENT DOCUMENTS

2008/0039723 A1 * 2/2008 Suri ..................... A61B 8/0833
600/437
2009/0028397 A1    1/2009 Makram-Ebeid
(Continued)

OTHER PUBLICATIONS

Rusu et al., "Prostatome: A combined anatomical and disease based MRI atlas of the prostate", Medical Physics, vol. 41, No. 7, Jun. 17, 2014. (Year: 2014).*
(Continued)

*Primary Examiner* — Vu Le
*Assistant Examiner* — Julius Chai
(74) *Attorney, Agent, or Firm* — O'Banion & Ritchey LLP; John P. O'Banion

(57) ABSTRACT

A probability map of prostate tumor location is generated and displayed in response to receiving anatomic diagnostic medical imaging, such as from magnetic resonance (MR) scanning. A registration process is performed on the images in relation to a model built of prostate anatomy across different subjects in an enhanced prostate template. A probability map is created of tumor locations followed by transforming the imaging to incorporate the probability map and output a resultant image.

24 Claims, 5 Drawing Sheets

Related U.S. Application Data

(60) Provisional application No. 62/567,290, filed on Oct. 3, 2017.

(51) Int. Cl.
*G06T 7/33* (2017.01)
*A61B 5/00* (2006.01)
*A61B 5/055* (2006.01)
*G01R 33/56* (2006.01)
*G06T 11/00* (2006.01)

(52) U.S. Cl.
CPC ........ *A61B 5/4887* (2013.01); *G01R 33/5602* (2013.01); *G01R 33/5608* (2013.01); *G06T 7/143* (2017.01); *G06T 7/337* (2017.01); *G06T 11/006* (2013.01); *G06T 2207/10088* (2013.01); *G06T 2207/30081* (2013.01); *G06T 2207/30096* (2013.01)

(58) Field of Classification Search
CPC . G06T 2207/10081; G06T 2207/30004; G06T 2207/30081; G06T 2207/30096; A61B 5/004; A61B 5/055; A61B 5/4381; A61B 5/4887; G01R 33/5602; G01R 33/5608
See application file for complete search history.

(56) References Cited

U.S. PATENT DOCUMENTS

| | | |
|---|---|---|
| 2009/0048515 A1 | 2/2009 | Suri |
| 2011/0306043 A1 | 12/2011 | Fuchs |
| 2012/0320055 A1* | 12/2012 | Pekar .................... G06T 7/143 345/424 |
| 2016/0086326 A1 | 3/2016 | Raschke |
| 2016/0350946 A1 | 12/2016 | Schieke |

OTHER PUBLICATIONS

Rusu, Mirabela et al., "Prostatome: A combined anatomical and disease based MRI atlas of the prostate", Medical Physics, vol. 41, No. 7, pp. 072301-1 to 072301-12, published Jun. 17, 2014.

Nagarajan, Mahesh B. et al., "Building a high-resolution T2-weighted MR-based proabilisitic model of tumor occurrence in the prostate", Abdominal Radiology, vol. 43, No. 9, pp. 2487-2496, published online Feb. 19, 2018.

European Patent Office, Communication (extended European search report) dated Feb. 15, 2021, related EPO application No. 18864794. 5, pp. 1-9, claims searched, pp. 10-14.

ISA/US, United States Patent and Trademark Office (USPTO), International Search Report and Written Opinion dated Dec. 20, 2018, related PCT international application No. PCT/US2018/053898, pp. 1-10, claims searched, pp. 11-15.

Abd-Alazeez, Mohamed et al., "The accuracy of multiparametric MRI in men with negative biopsy and elevated PSA level—Can it rule out clinically significant prostate cancer?", Urol Oncol. Jan. 2014; 32(1): 45.e17-45.e22, published online Sep. 18, 2013.

Narayanan, Ramkrishnan et al., "Application of statistical cancer atlas for 3D biopsy", Conference Paper in Proceedings of SPIE, The International Society for Optical Engineering 6812:681216, Feb. 2008.

European Patent Office (EPO), Communication pursuant to Article 94(3) EPC dated Jan. 12, 2022, related European patent application No. 18 864 794.5, pp. 1-6, claims examined, 7-10.

* cited by examiner

APPARATUS AND METHOD FOR DETERMINING THE SPATIAL PROBABILITY OF CANCER WITHIN THE PROSTATE

This application claims priority to, and is a 35 U.S.C. § 111(a) continuation of, PCT international application number PCT/US2018/053898 filed on Oct. 2, 2018, incorporated herein by reference in its entirety, which claims priority to, and the benefit of, U.S. provisional patent application Ser. No. 62/567,290 filed on Oct. 3, 2017, incorporated herein by reference in its entirety. Priority is claimed to each of the foregoing applications.

The above-referenced PCT international application was published as PCT International Publication No. WO 2019/070658 A1 on Apr. 11, 2019, which publication is incorporated herein by reference in its entirety.

STATEMENT REGARDING FEDERALLY SPONSORED RESEARCH OR DEVELOPMENT

Not Applicable

NOTICE OF MATERIAL SUBJECT TO COPYRIGHT PROTECTION

A portion of the material in this patent document may be subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

The technology of this disclosure pertains generally to analyzing and enhancing diagnostic medical images, and more particularly to probability mapping of tumor locations in diagnostic medical imaging of the prostate.

2. Background Discussion

Substantial evidence has been documented in patients with prostate and other types of cancer, that biopsies using imaging techniques are critical toward providing accurate diagnosis and implementation of radiation therapy protocols. Magnetic resonance imaging (MRI), or MRI fused with ultrasound mapping, or High Resolution Computed Tomography (HRCT), are popular methods used for directing biopsy locations. The challenge in biopsy of patients with possible cancer is to confidently identify appropriate lesions with moderate to high grade cancer and to be certain where the biopsies were taken, when compared to pathology results, which include not only histology, but will include a variety of molecular and genomic markers.

Accordingly, a need exists for a method and apparatus to improve cancer probability mapping of the prostate. The present disclosure fulfills that need and provides additional benefits over previous technologies.

BRIEF SUMMARY

This disclosure describes a method for generating a probability map on a high-resolution anatomic image, including but not limited to, MR (magnetic resonance) images, that indicates the probability of cancer at any anatomical location. In general terms, the method involves (1) image registration, and (2) probability map creation. Further aspects of the technology described herein will be brought out in the following portions of the specification, wherein the detailed description is for the purpose of fully disclosing preferred embodiments of the technology without placing limitations thereon.

Further aspects of the technology described herein will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

DETAILED DESCRIPTION

A method is described for generating a probability map on high resolution diagnostic anatomical imaging, such as magnetic resonance (MR) imaging, that provides probability mapping of cancer.

1. Imaging System Enhanced for Spatial Cancer Probability

Figure 1:
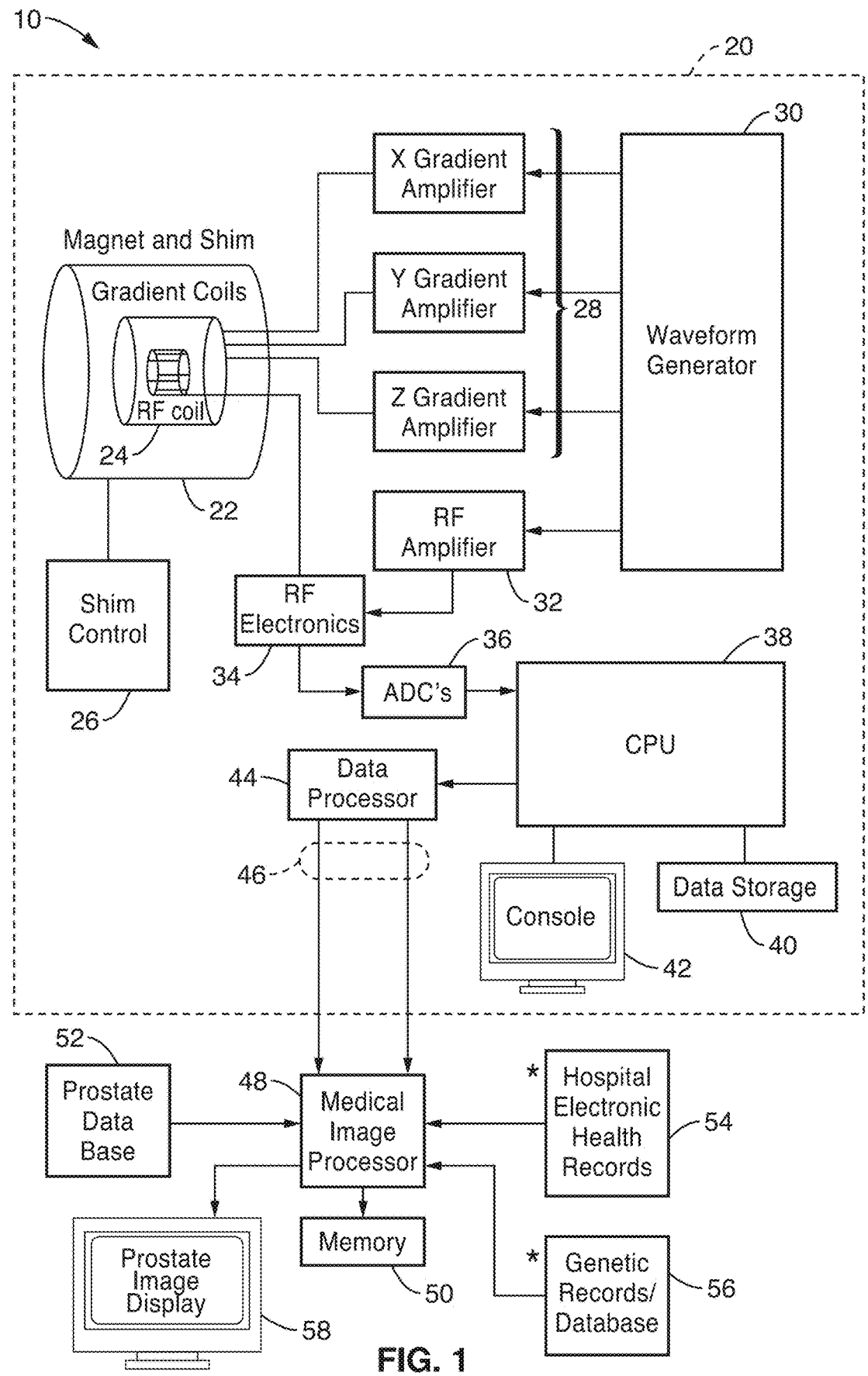
FIG. 1 is a block diagram of medical scanning system configured for determining spatial probability of cancer within the prostate.

FIG. 1 is an example embodiment 10 of the apparatus for determining spatial probability of cancer in response to augmented medical imaging. The disclosed apparatus and method is configured for integration with, or within, medical imaging devices which can be utilized for cancer patient imaging. These imaging systems may comprise, Magnetic Resonance Imaging (MRI), Computed Tomography (CT), High Resolution Computed Tomography (HRCT), Molecular and Nuclear Imaging (PET and SPECT), and others capable of providing imaging for prostate cancer. By way of example and not limitation, much of the discussion is directed at magnetic resonance imaging.

An MRI system 20 is shown with its magnet and shim 22, gradient coils 24, shim control 26, gradient amplifiers 28, waveform generation 30, RF amplifier 32, RF sensing electronics 34, and analog-to-digital conversion 36. The scanning of the imaging is controlled by a processor 38 coupled to data storage 40 and controlled through console 42. A data processor 44 in the system is configured for outputting image data and metadata 46 to a medical imaging processing station 48 coupled to memory 50. It should be appreciated that other systems utilized for diagnostic cancer imaging, have similar outputs for scan image data and metadata 46, which is directed to medical imaging processing station 48, and associated memory 50. The medical imaging processing station 48 incorporates one or more processors, and is coupled for receiving additional information from a clinical data base 52 of prostate information, and preferably hospital electronic health records 54, and genetic records/database 56, both of which provide information on conditional factors (e.g., age, mutation status) for modifying the disclosed cancer probability maps. The ability to extract descriptive information about prostate related lesions from a clinical database is crucial for the present system in tailoring its population mapping for specific needs/applications. For example instances arise when population maps are built of tumors on different sub-populations, as stratified by demographics, clinical scores (e.g., PSA), pathological findings (e.g., Gleason scores), molecular profiles, and other factors across one or more demographics. In response to methods described in a later section, this information is utilized to enhance prostate cancer imaging and output 58 spatial probability on medical imaging as determined during medical scanning.

Returning to FIG. 1 it will be noted that signals 46 obtained from the medical imaging scanner, provide data about the medical imaging scanning process as a combination of images and information about the scan, which will be generally referred to as metadata. In the case of the exemplified MRI system, and similar systems, this medical scan data is acquired from the imaging scanner in DICOM (Digital Imaging and Communication in Medicine) format. This format allows transmission of both image data and additional metadata relevant to the image data being transmitted and archived. The metadata (also known as DICOM header) includes a significant amount of information in regards to both image identification and registration, wherein the following is only provided by way of example, and not limitation.

In regards to image identification, identifiers such as patient ID, study date, and accession number are used to associate the images with the correct subject being included in the population map. Series instance UID is a universal identifier that further helps the present system identify the specific series which is to be contoured and processed in a probability map being output according to the present disclosure. In addition, other imaging sequence identifiers or acquisition parameters can be communicated, such as modality, sequence protocol name, series description, and so forth, which can aid the system in identifying correct sets of images to process for inclusion in its population map building processes.

In regards to registration, a series of 2D DICOM images characterize the volume of the prostate. When registering a candidate prostate volume to the prostate template model, it is very important to have quantifiable dimensions of the candidate prostate volume. For instance 20 images of 256 rows and 256 columns will cover the entire prostate, yet having just images alone indicates nothing about the size or orientation of the prostate volume that is captured by these images. The above information is captured in the DICOM header. The physical space occupied by each individual pixel is stored in the DICOM header (also known as in pixel resolution), which determines the actual physical space occupied by a single slice. Similarly, the origin of each slice as well its perpendicular vector are also stored in the DICOM header. This allows the disclosed system to understand the spatial relationship between different slices. Together, this information allows quantifications of the actual dimensions of the prostate volume in the real world. It will be appreciated that knowing a prostate volume is 120 cc is clinically significant, while knowing it was imaged containing 198 pixels/voxels would not of itself provide a discriminating factor in assessing cancer in a specific prostate. This information is crucial for the registration step where the prostate is transformed into the space of the prostate template by the disclosed apparatus and method.

In a generalized embodiment the method comprises the following steps: (1) image registration, and (2) probability map creation. Each of the foregoing steps is described in detail below.

2. Image Registration

Figure 2:
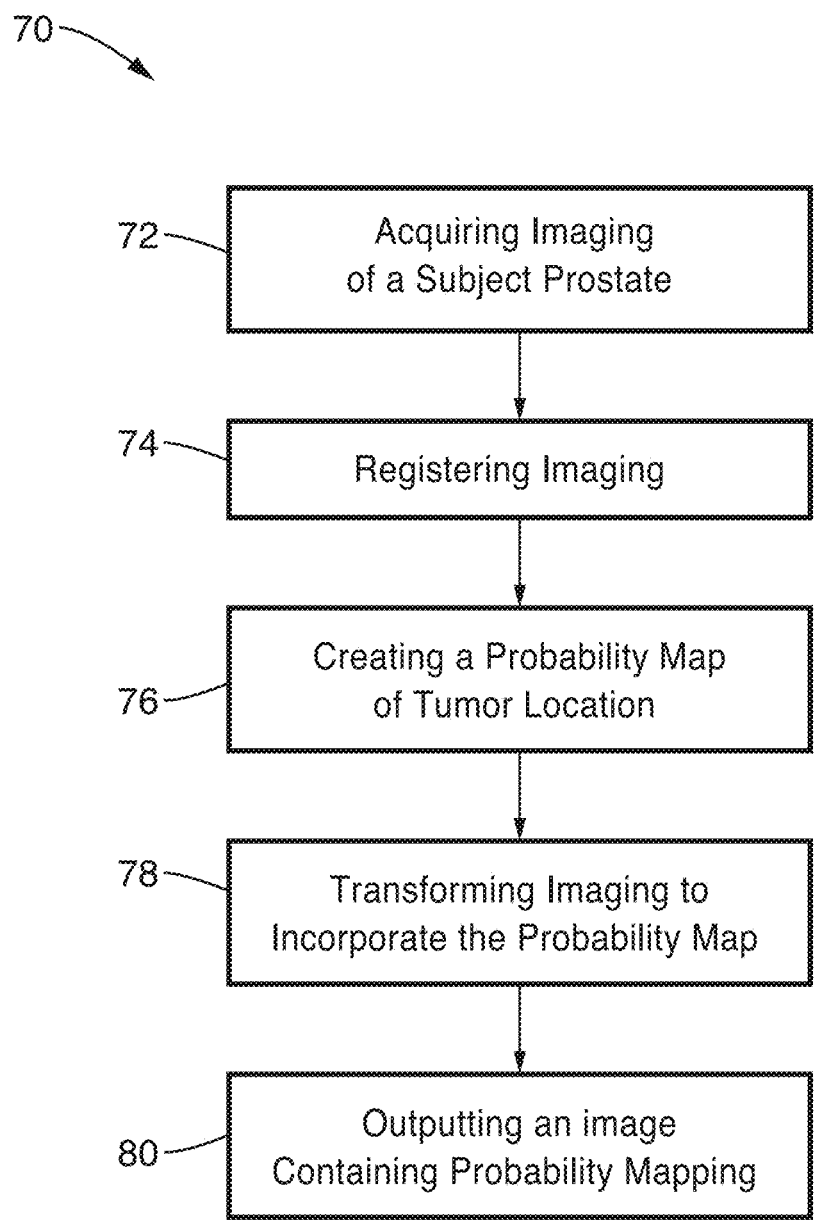
FIG. 2 is a flow diagram of a method for generating a probability map of a tumor location according to an embodiment of the present disclosure.

FIG. 2 illustrates an example embodiment 70 of generating a probability map based on medical scan imaging data 72, such as from magnetic resonance (MR), or other scanning technology suitable for cancer imaging. The basic steps in processing this imaging data comprise registering scanner images 74, creating a probability map of tumor location 76, transforming 78 the scanner imaging to incorporate the probability map, then outputting 80 enhanced scanner images incorporating the disclosed probability mapping. These steps are described in greater detail in the following sections.

The first step in tumor probabilistic model building in the prostate is the registration 74 of prostate anatomy across different subjects to the space of a common template. It should be appreciated that the term 'registration' as utilized herein refers to registering images in an alignment process so that common features overlap, whereby any differences are emphasized and made more readily visible.

Figure 3:
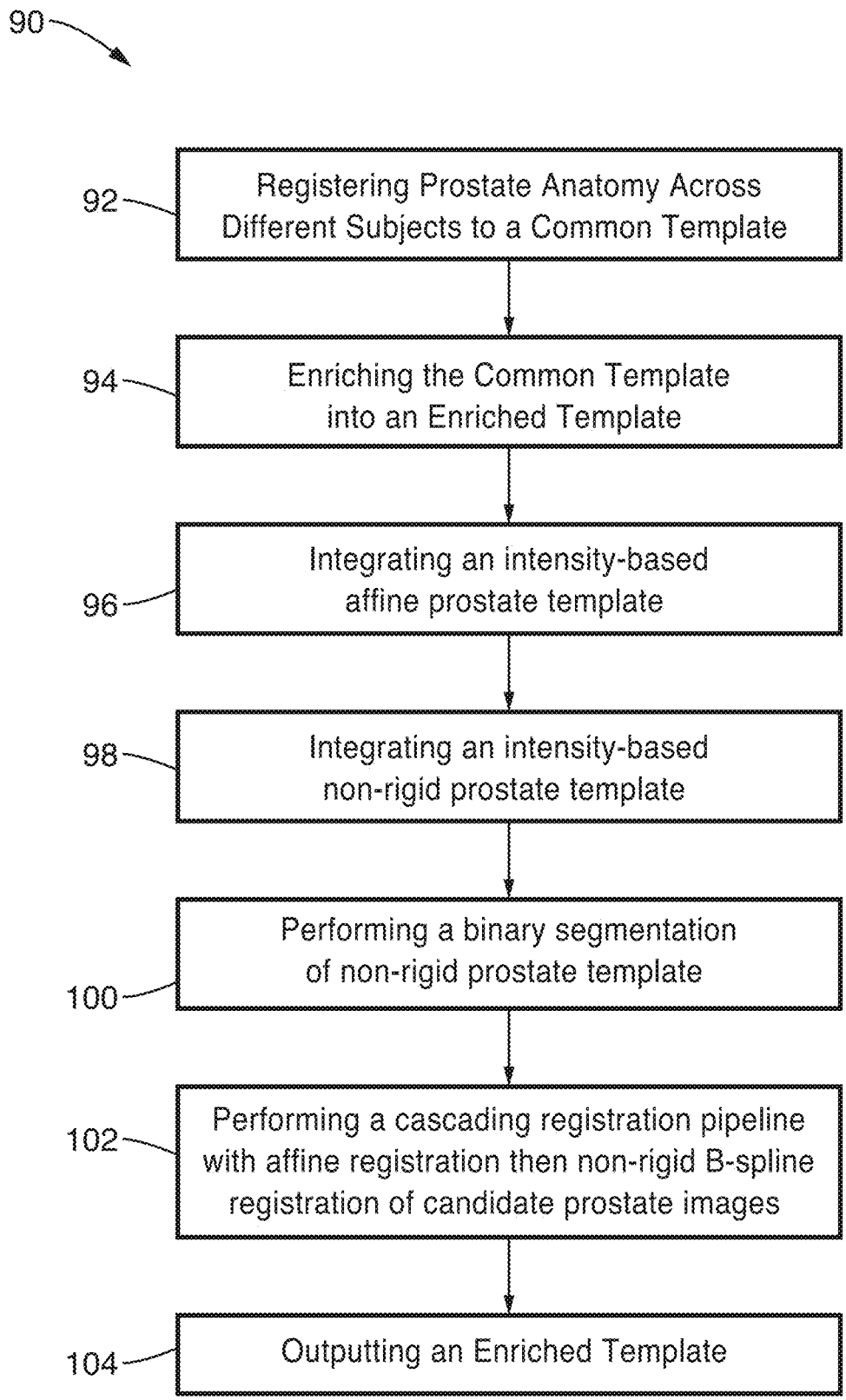
FIG. 3 is a flow diagram of generating an enriched prostate template according to an embodiment of the present disclosure.

FIG. 3 illustrates an example embodiment 90 of steps in creating an enriched prostate template. Prostate anatomy is registered across different subjects to a common template 92, then this common template is enriched 94 in a process of integrating 96 an intensity-based affine prostate template, integrating 98 an intensity-based non-rigid prostate template, performing 100 a binary segmentation of non-rigid prostate template, performing 102 a cascading registration pipeline with affine registration then non-rigid B-spline registration of candidate prostate images, followed by outputting 104 an enriched template. The following describes these elements in greater detail.

In the context of MR images, high resolution T2-weighted (T2 is the relaxation time of tissues) MR images are utilized and the corresponding prostate segmentation for every subject, to perform a registration framework for the present disclosure which uses an enriched template which incorporates the following component templates: (1) an intensity-based affine prostate template, (2) an intensity-based non-rigid prostate template, (3) a binary segmentation of the non-rigid prostate template, and (4) a cascading registration pipeline involving affine registration followed by a non-rigid B-spline registration of candidate prostate images to the enriched template.

This enriched prostate template model is constructed from a random subset of candidate prostates. The number of prostates used is a parameter in the model. A randomly chosen candidate from this subset serves as an initial template; then other candidate prostates are registered through a cascaded application of affine and non-rigid B-spline transformations. The average deformation field is then computed and applied to all candidates in this subset, with the final enriched prostate template being derived from their median intensities. The average deformation field is also applied to the prostate segmentation for all candidate prostates in the subset, with an enriched template mask being identified as regions where at least 50% of the deformed candidate prostate segmentations overlap.

Figure 4:
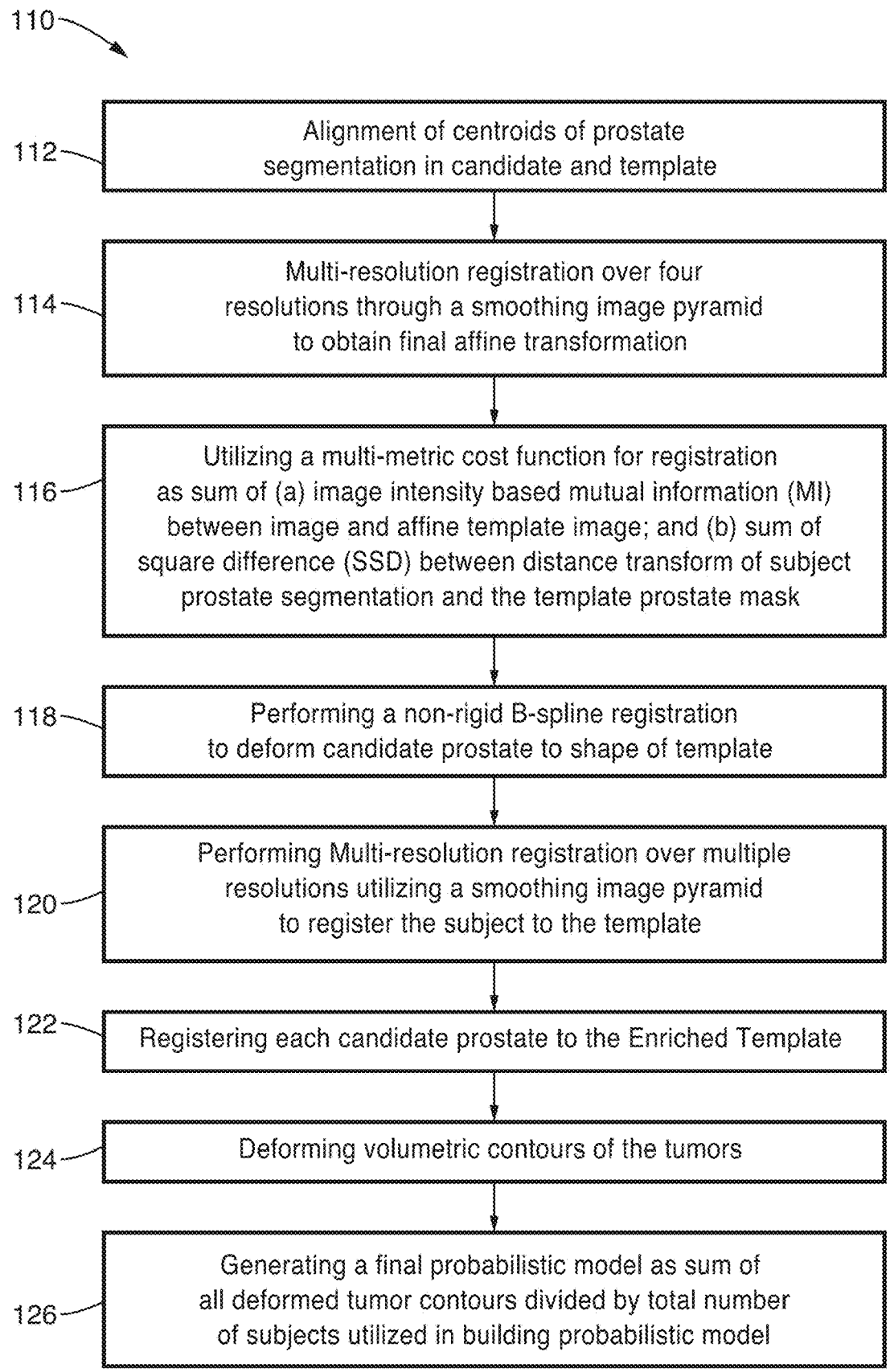
FIG. 4 is a flow diagram of registering a candidate prostate to the enriched prostate template according to an embodiment of the present disclosure.

FIG. 4 illustrates an example embodiment 110 of registering the candidate prostate to the enhanced prostate template. Once the enhanced template is created, the candidate prostate and its corresponding segmentation are affinely registered to the enhanced prostate template and its prostate segmentation. The registration process is initialized with alignment 112 of the centroids of the prostate segmentation in the candidate and template to improve the performance of the affine registration step. Multi-resolution registration is performed 114, such as by way of example over four resolutions, through a smoothing image pyramid is then performed to obtain the final affine transformation. A multimetric cost function 116 is utilized for the registration, which in this example comprises the sum of the following two components: (a) image intensity based mutual information (MI) between the image (e.g., T2 image) and the affine template image; and (b) sum of square difference (SSD) between the distance transform of the subject prostate segmentation and the template prostate mask.

The affine registration is subsequently followed by a non-rigid B-spline registration 118 where the candidate prostate is deformed to the same shape as the template. Multi-resolution registration 120 is again performed over multiple (e.g., four) resolutions through a smoothing image pyramid to register the subject to the template, where the intensity-based mutual information of the mask images is used as the cost function.

All registration operations in the present disclosure operate in response to first converting image data from voxel coordinates (determined from the volume dimensions—rows, columns and number of slices which are themselves dimensionless, i.e., have no unit) to real world coordinates (i.e., physical coordinates which have a unit of millimeters). This conversion is achieved through the use of the DICOM patient position and orientation attributes, with the patient position yielding the origin of each 2D slice, and the patient orientation characterizing the vector normal of each slice. Additionally, the DICOM pixel spacing attribute further assists in characterizing the coordinates of each pixel in mm.

Using the enriched prostate template model and the inter-subject prostate registration described above, each available candidate prostate is registered 122 to the template. Volumetric contours of the tumors (both true and false positives with respect to pathology) are then deformed 124 using the corresponding transformations computed from the registration process. The final probabilistic model is generated 126 as the sum of all deformed tumor contours divided by the total number of subjects used to build the probabilistic model.

3. Probability Map Creation

Referring back to FIG. 2, in this next step a probability map is created 76 of tumor location. Let the frequency of localized target lesion from the registered map by Gleason score be $p_{ij}$ where for example i=3+3, 3+4, 4+3 and the sum being greater than or equal to 8; with j as the registered co-ordinate of an (x, y, z) location. Each $p_{ij}$ has a distribution of malignant f ($p_{ij}$) or benign g ($p_{ij}$) from the population map with an intensity or normalized intensity, such as from a magnetic resonance (MR) T2 weighted (highlighting differences in the T2 relaxation time of tissues) three-dimensional (3D) space model. Per each voxel ($q_{ij}$) from a new MR image, a percentile of distance of distribution for each voxel being malignant or benign can be derived with multiple types (e.g., four (4)) of Gleason score, such as (3+3, 3+4, 4+3,≥8). Then choosing max $q_{ij}$=maximum (percentile of malignant f ($p_{ij}$), percentile of benign g ($p_{ij}$) per Gleason type, which is set to P (cancerous cell at local clinic level). Upon the availability of genetic radiomic pathologic markers, the likelihood function is then estimated. The posterior probability will be estimated from the prior model in image registration and the likelihood model of the radiomic pathological marker.

The probability of distance map of voxels being malignant per Gleason type is represented as follows.

$$\text{Predictive\_Probability}(\text{malignant\_scores}) =$$
$$P(\text{cancerous\_cell} \mid \text{radiometric\_pathologic\_markers}) =$$
$$P(\text{cancerous\_cell}_{local\_clinic\_level}) *$$
$$\text{likelihood}(\text{cancerous\_cell, genetic\_radiomic\_pathologic\_markers})$$

Table 1 provides an example of pseudo code (using Winbug functional code) for determining the Predictive Probability. The examples illustrate three markers (Marker 1, Marker 2, & Marker 3) and Probability of a cancer cell (PCC); probability depends on data and a random effect; Predictive Probability (PPOS). The code estimates the posterior probability of the model. When the locations of predictive probability (malignant scores) forms a cluster with at least twice the size of variation, the system outputs the likelihood of malignant score.

Table 2 provides an example of source code (pseudo-code in an executable pseudo-code (Python)) for population map building (prostate registration pipeline).

4. Tumor Probability Mapping Example 1.

Figure 5:
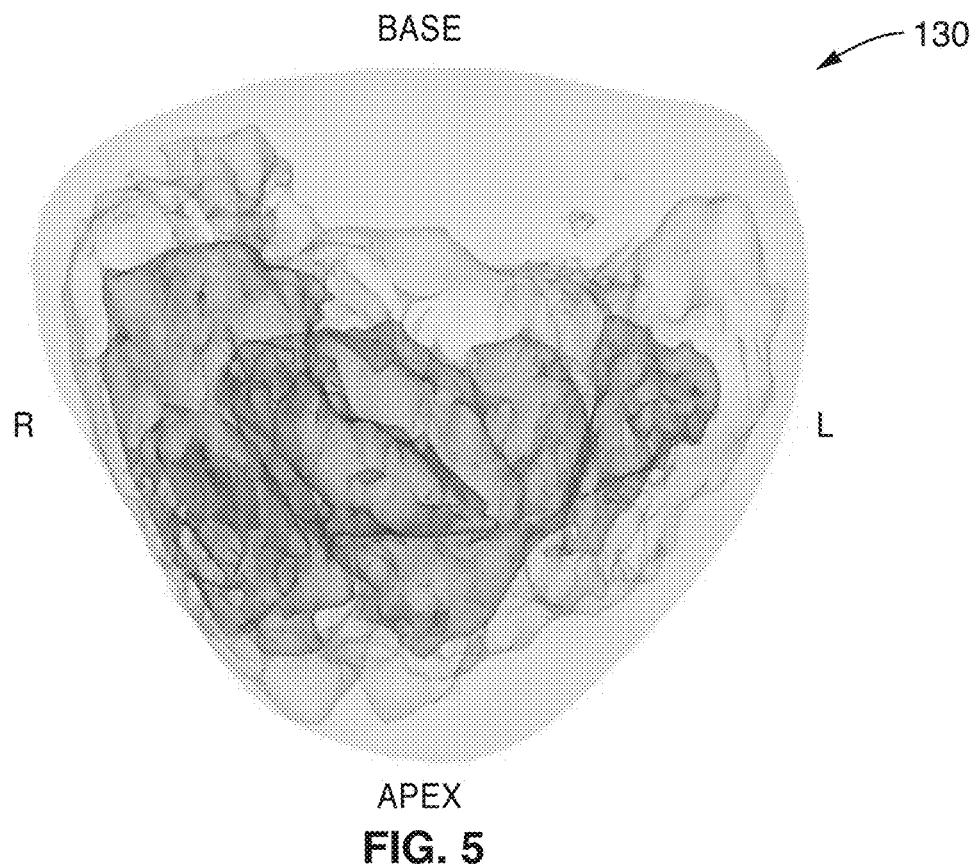
FIG. 5 is a probability map of index tumors (clinically most significant tumor found in a prostate) as generated according to an embodiment of the present technology.

FIG. 5 illustrates an example embodiment 130 showing a resultant probability map of index tumors (clinically most significant tumor found in a prostate) as built through the approach described herein. This particular map was built using 206 index tumors extracted from high resolution T2 MR scans of 240 subjects. It will be noted that the images attached are monochrome due to current patent office limitations. The present disclosure, however, outputs the map of index tumors in a color coded manner, using any desired color(s) to represent any class of object. By way of example and not limitation, the color code is as follows: Red:≥20 lesions, Yellow: 15-19 lesions, Blue: 10-14 lesions, White: 5-9 lesions, and no color for 1-5 lesion areas toward improved visualization. Of particular interest are the hot spots in red, where the frequency of clinically significant tumor occurrence is the largest.

5. Tumor Probability Mapping Example 2.

Figure 6:
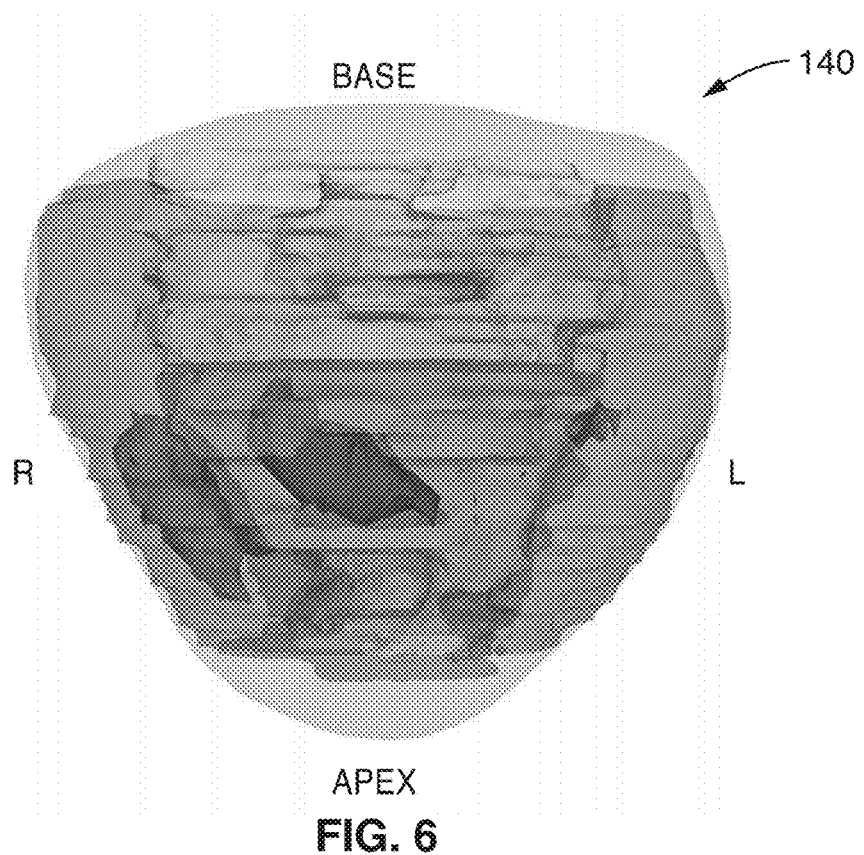
FIG. 6 is a probability map on locations of the hot spots identified in FIG. 5 with respect to the internal anatomy of the prostate.

FIG. 6 illustrates an example embodiment 140 showing locations of hot spots identified in FIG. 5 with respect to the internal anatomy of the prostate. Again, it will be noted that the FIG. 6 image is in a monochrome format due to current patent office limitations. By way of example and not limitation on color choices, this particular map was created showing the peripheral zone in pink, the transition zone in yellow, the central zone in green and the anterior fibromuscular stroma in blue. The hotspots, areas where a plurality (e.g., 15 or more in this case) index tumors were observed, is indicated in another color (e.g., red in this case). These hotspots are observed in the posterior peripheral and anterior peripheral or transition zones.

6. Expected Technology Utilization.

This technology can be utilized to list localized target lesions from patients who undergo biopsy. In addition, this technology can be utilized in a number of different settings, including both routine clinical practice or in clinical trials.

In one embodiment, the method is implemented as part of a system using computer software run on an individual medical imaging workstation, by the image acquisition device, or on a reading workstation. The software can also be run on a centralized server or cluster of servers in a radiology department or medical center. Running on a server may offer some advantages in terms of interfacing with a centralized imaging archive, and storing reports in a centralized database. The system can also be accessed remotely, via the internet for example, or using GRID computing. Using this latter approach, the system can be made available as a GRID service, and clients with proper authentication/authorization can access it world-wide.

7. General Scope of Embodiments

The enhancements described in the presented technology can be readily implemented within various medical imaging workstations (individually, or on a centralized server or cluster of servers) configured with one or more computer processor devices (e.g., CPU, microprocessor, and so forth) and associated memory storing instructions (e.g., RAM, DRAM, NVRAM, FLASH, computer readable media, etc.) whereby programming (instructions) stored in the memory are executed on the processor to perform the steps of the various process methods described herein.

The computer and memory devices were not depicted in the diagrams for the sake of simplicity of illustration, as one of ordinary skill in the art recognizes the use of computer devices for carrying out steps involved with medical imaging analysis. The presented technology is non-limiting with regard to memory and computer-readable media, insofar as these are non-transitory, and thus not constituting a transitory electronic signal.

Embodiments of the present technology may be described herein with reference to flowchart illustrations of methods and systems according to embodiments of the technology, and/or procedures, algorithms, steps, operations, formulae, or other computational depictions, which may also be implemented as computer program products. In this regard, each block or step of a flowchart, and combinations of blocks (and/or steps) in a flowchart, as well as any procedure, algorithm, step, operation, formula, or computational depiction can be implemented by various means, such as hardware, firmware, and/or software including one or more computer program instructions embodied in computer-readable program code. As will be appreciated, any such computer program instructions may be executed by one or more computer processors, including without limitation a general purpose computer or special purpose computer, or other programmable processing apparatus to produce a machine, such that the computer program instructions which execute on the computer processor(s) or other programmable processing apparatus create means for implementing the function(s) specified.

Accordingly, blocks of the flowcharts, and procedures, algorithms, steps, operations, formulae, or computational depictions described herein support combinations of means for performing the specified function(s), combinations of steps for performing the specified function(s), and computer program instructions, such as embodied in computer-readable program code logic means, for performing the specified function(s). It will also be understood that each block of the flowchart illustrations, as well as any procedures, algorithms, steps, operations, formulae, or computational depictions and combinations thereof described herein, can be implemented by special purpose hardware-based computer systems which perform the specified function(s) or step(s), or combinations of special purpose hardware and computer-readable program code.

Furthermore, these computer program instructions, such as embodied in computer-readable program code, may also be stored in one or more computer-readable memory or memory devices that can direct a computer processor or other programmable processing apparatus to function in a particular manner, such that the instructions stored in the computer-readable memory or memory devices produce an article of manufacture including instruction means which implement the function specified in the block(s) of the flowchart(s). The computer program instructions may also be executed by a computer processor or other programmable processing apparatus to cause a series of operational steps to be performed on the computer processor or other programmable processing apparatus to produce a computer-implemented process such that the instructions which execute on the computer processor or other programmable processing apparatus provide steps for implementing the functions specified in the block(s) of the flowchart(s), procedure(s) algorithm(s), step(s), operation(s), formula(e), or computational depiction(s).

It will further be appreciated that the terms "programming" or "program executable" as used herein refer to one or more instructions that can be executed by one or more computer processors to perform one or more functions as described herein. The instructions can be embodied in software, in firmware, or in a combination of software and firmware. The instructions can be stored local to the device in non-transitory media, or can be stored remotely such as on a server, or all or a portion of the instructions can be stored locally and remotely. Instructions stored remotely can be downloaded (pushed) to the device by user initiation, or automatically based on one or more factors.

It will further be appreciated that as used herein, that the terms processor, hardware processor, computer processor, central processing unit (CPU), and computer are used synonymously to denote a device capable of executing the instructions and communicating with input/output interfaces and/or peripheral devices, and that the terms processor, hardware processor, computer processor, CPU, and computer are intended to encompass single or multiple devices, single core and multicore devices, and variations thereof.

From the description herein, it will be appreciated that the present disclosure encompasses multiple embodiments which include, but are not limited to, the following:

1. An apparatus for generating a probability map of a tumor location on an diagnostic medical imaging of a prostate, the apparatus comprising: (a) a processor; and (b) a non-transitory computer-readable memory storing instructions executable by the processor; (c) wherein said instructions, when executed by the processor, perform steps comprising: (c)(i) acquiring diagnostic medical imaging and metadata from medical imaging of a prostate; (c)(ii) obtaining prostate information from a clinical database; (c)(iii) registering the diagnostic medical imaging image; (c)(iv) creating a probability map of tumor location; and (c)(v) transforming the diagnostic medical images and probability map into an output image incorporating the probability map on the diagnostic medical image.

2. The apparatus or method of any preceding or following embodiment, wherein said instructions when executed by the processor performs registering the diagnostic medical imaging comprising registering the prostate across multiple subjects to the space of a common template.

3. The apparatus or method of any preceding or following embodiment, wherein said diagnostic medical imaging comprises T2-weighted magnetic resonance (MR) images.

4. The apparatus or method of any preceding or following embodiment, wherein said instructions when executed by the processor performs registering the diagnostic medical imaging further comprising: (a) using high resolution and corresponding segmentation of the prostate for every subject; (b) constructing an enriched prostate template from a subset of candidate prostates; and (c) generating a registration framework based on the enriched prostate template.

5. The apparatus or method of any preceding or following embodiment, wherein said instructions when executed by the processor generates the enriched prostate template comprising: (a) an intensity-based affine prostate template; (b) an intensity-based non-rigid prostate template; (c) a binary segmentation of the non-rigid prostate template; and (d) a cascading registration pipeline involving affine registration followed by a non-rigid B-spline registration of candidate prostate images to the enriched template.

6. The apparatus or method of any preceding or following embodiment, wherein said instructions when executed by the processor performs registering the diagnostic medical imaging which further comprises: (a) utilizing a randomly chosen candidate from the subset of candidate prostates as an initial template; and (b) registering other candidate prostates through a cascaded application of affine and non-rigid B-spline transformations.

7. The apparatus or method of any preceding or following embodiment, wherein said instructions when executed by the processor perform said registering the diagnostic medical imaging which further comprises: (a) computing an average deformation field; and (b) applying the average deformation field to all candidates in the subset of candidate prostates.

8. The apparatus or method of any preceding or following embodiment, wherein said instructions when executed by the processor performs said registering the diagnostic medical imaging which further comprises deriving a final enriched prostate template from median intensities of the subset of candidate prostates.

9. The apparatus or method of any preceding or following embodiment, wherein said instructions when executed by the processor perform said registering the diagnostic medical imaging which further comprises identifying an enriched prostate template mask as regions where at least 50% of deformed candidate prostate segmentations overlap.

10. The apparatus or method of any preceding or following embodiment, wherein said instructions when executed by the processor perform registering of the diagnostic medical imaging which further comprises (a) creating a prostate template, and (b) affinely registering the candidate prostate and its corresponding segmentation to the prostate template and its prostate segmentation.

11. The apparatus or method of any preceding or following embodiment, wherein said instructions when executed by the processor perform said registering the diagnostic medical imaging which further comprises initializing the registration process with alignment of centroids of the prostate segmentation in the candidate and template to improve performance of the affine registration step.

12. The apparatus or method of any preceding or following embodiment, wherein said instructions when executed by the processor perform said registering the diagnostic medical imaging which further comprises obtaining a final affine transformation by performing multi-resolution registration over four resolutions through a smoothing image pyramid.

13. The apparatus or method of any preceding or following embodiment, wherein said registering the diagnostic medical imaging further comprises using a multi-metric cost function for the registration, with the cost function comprising (a) image intensity based mutual information (MI) between the T2 image and the affine template image; and (b) sum of square difference (SSD) between the distance transform of the subject object segmentation and the template prostate mask.

14. The apparatus or method of any preceding or following embodiment, wherein said instructions when executed by the processor perform said registering the diagnostic medical imaging which further comprises performing a non-rigid B-spline registration in which a candidate object is deformed to the same shape as prostate template.

15. The apparatus or method of any preceding or following embodiment, wherein said instructions when executed by the processor perform said registering the diagnostic medical imaging which further comprises: (a) performing multi-resolution registration over four resolutions through a smoothing image pyramid to register a subject diagnostic medical imaging to a prostate template, and (b) utilizing intensity-based mutual information of the mask images is as a cost function.

16. The apparatus or method of any preceding or following embodiment, wherein said instructions when executed by the processor perform said registering the diagnostic medical imaging which further comprises registering each available candidate object to a prostate template using an enriched prostate template model and inter-subject object registration.

17. The apparatus or method of any preceding or following embodiment, wherein said instructions when executed by the processor perform said registering the diagnostic medical imaging which further comprises deforming volumetric contours of tumors, including both true and false positives with respect to pathology, utilizing corresponding transformations computed from registering the diagnostic medical imaging.

18. The apparatus or method of any preceding or following embodiment, wherein said instructions when executed by the processor perform said registering the diagnostic medical imaging which further comprises building a final probabilistic model from a sum of all deformed tumor contours divided by a total number of prostate subjects.

19. The apparatus or method of any preceding or following embodiment, wherein said instructions when executed by the processor perform said creating a probability map of tumor location further comprises designating a location in the diagnostic medical imaging as probable of being malignant when locations of predictive probability, including malignant scores, form a cluster as an estimate.

20. The apparatus or method of any preceding or following embodiment, wherein the predictive probability of malignant scores is determined by the probability of cancerous cell of a tumor location given genetic, radiologic, and pathologic markers from a subject or a tumor lesion.

21. The apparatus or method of any preceding or following embodiment, wherein the predictive probability of malignant scores is determined by the product of two parts:

(a) the prior knowledge of a prevalence of a specific type of cancer at local clinical level; and (b) the likelihood function of the joint distribution of the location of cancerous cell of tumor, genetic, radiomic, and pathologic markers from subject or a tumor lesion.

22. The apparatus or method of any preceding or following embodiment, wherein said instructions when executed by the processor perform said creating a probability map of tumor location further comprises designating a location in the diagnostic medical imaging as probable of being malignant when locations of predictive probability, including malignant scores, form a cluster as well as provide a confidence bound around a tumor.

23. The apparatus or method of any preceding or following embodiment, wherein a confidence interval of predictive probability of malignant scores is determined by the probability of cancerous cells of a tumor given occurrence of genetic, radiomic, and pathologic markers from a subject or a tumor lesion.

24. The apparatus or method of any preceding or following embodiment, wherein said confidence interval of predictive probability, including malignant scores, is determined by the product of two parts: (a) prior knowledge of a prevalence of a specific type of cancer at a local clinical level; and (b) a likelihood function of a joint distribution of cancerous cell of tumor, genetic, radiomic, and pathologic markers from a subject or a tumor lesion.

25. A method of generating a probability map of a tumor location on diagnostic medical imaging of a prostate, comprising: (a) acquiring diagnostic medical imaging and metadata from medical image scanning of a prostate; (b) obtaining prostate information from a clinical database; (c) registering the diagnostic medical imaging image; (d) creating a probability map of tumor location; and (e) transforming the diagnostic medical images and probability map into an output image incorporating the probability map on the diagnostic medical image.

26. An apparatus for generating a probability map of a tumor location on an MR image of a prostate, the apparatus comprising: (a) a computer processor; and (b) a non-transitory computer-readable memory storing instructions executable by the computer processor; (c) wherein said instructions, when executed by the computer processor, perform steps comprising: (c)(i) acquiring an input MR image of a prostate; (c)(ii) registering the MR image; (c)(iii) creating a probability map of a tumor location; and (c)(iv) transforming the MR image and probability map into an output image showing the probability map on the MR image.

27. The apparatus or method of any preceding or following embodiment, wherein said registering the MR image comprises: registering the prostate across multiple subjects to the space of a common template.

28. The apparatus or method of any preceding or following embodiment, wherein said registering the MR image further comprises: using high resolution T2-weighted MR images and corresponding segmentation of the prostate for every subject; constructing an enriched prostate template from a subset of candidate prostates; and developing a registration framework which uses the enriched template.

29. The apparatus or method of any preceding or following embodiment, wherein the enriched template comprises: (a) an intensity-based affine prostate template; (b) an intensity-based non-rigid prostate template; (c) a binary segmentation of the non-rigid prostate template; and (d) a cascading registration pipeline involving affine registration followed by a non-rigid B-spline registration of candidate prostate images to the enriched template.

30. The apparatus or method of any preceding or following embodiment, wherein said registering the MR image further comprises: using a randomly chosen candidate from the subset of candidate prostates as an initial template; and registering other candidate prostates through a cascaded application of affine and non-rigid B-spline transformations.

31. The apparatus or method of any preceding or following embodiment, wherein said registering the MR image further comprises: computing an average deformation field; and applying the average deformation field to all candidates in the subset of candidate prostates.

32. The apparatus or method of any preceding or following embodiment, wherein said registering the MR image further comprises: deriving a final enriched prostate template from median intensities of the subset of candidate prostates.

33. The apparatus or method of any preceding or following embodiment, wherein said registering the MR image further comprises: applying the average deformation field to the prostate segmentation for all candidate prostates in the subset.

34. The apparatus or method of any preceding or following embodiment, wherein said registering the MR image further comprises: identifying an enriched template mask as regions where at least 50% of the deformed candidate prostate segmentations overlap.

35. The apparatus or method of any preceding or following embodiment, wherein said registering the MR image further comprises: once the template is created, affinely registering the candidate prostate and its corresponding segmentation to the prostate template and its prostate segmentation.

36. The apparatus or method of any preceding or following embodiment, wherein said registering the MR image further comprises: initializing the registration process with alignment of centroids of the prostate segmentation in the candidate and template to improve performance of the affine registration step.

37. The apparatus or method of any preceding or following embodiment, wherein said registering the MR image further comprises: obtaining a final affine transformation by performing multi-resolution registration over four resolutions via a smoothing image pyramid.

38. The apparatus or method of any preceding or following embodiment, wherein said registering the MR image further comprises: using a multi-metric cost function for the registration, the cost function comprising: (a) image intensity based mutual information (MI) between the T2 image and the affine template image; and (b) sum of square difference (SSD) between the distance transform of the subject object segmentation and the template prostate mask.

39. The apparatus or method of any preceding or following embodiment, wherein said registering the MR image further comprises: performing a non-rigid B-spline registration where the candidate object is deformed to the same shape as the template.

40. The apparatus or method of any preceding or following embodiment, wherein said registering the MR image further comprises: performing multi-resolution registration is again performed over four resolutions via a smoothing image pyramid to register the subject to the template, wherein intensity-based mutual information of the mask images is used as the cost function.

41. The apparatus or method of any preceding or following embodiment, wherein said registering the MR image further comprises: registering each available candidate object to the template using the enriched prostate template model and the inter-subject object registration.

42. The apparatus or method of any preceding or following embodiment, wherein said registering the MR image further comprises: deforming volumetric contours of tumors (both true and false positives with respect to pathology) using the corresponding transformations computed from the registration process.

43. The apparatus or method of any preceding or following embodiment, wherein said registering the MR image further comprises: building a final probabilistic model from the sum of all deformed tumor contours divided by the total number of subjects.

44. The apparatus or method of any preceding or following embodiment, wherein said creating a probability map of a tumor location comprises: designating a location in the MR image as probable of being malignant when locations of predictive probability (malignant scores) form of a cluster with at least twice variation size.

45. The apparatus or method of any preceding or following embodiment, wherein the predictive probability is represented as: Predictive Probability (malignant scores)=P (cancerous cell|genetic radiomic pathologic markers).

46. The apparatus or method of any preceding or following embodiment, wherein the predictive probability is represented as: Predictive Probability (malignant scores)=P (cancerous cell at local clinic level)*likelihood(cancerous cell, genetic radiomic pathologic markers).

47. The apparatus or method of any preceding or following embodiment, wherein said creating a probability map of a tumor location comprises: designating a location in the MR image as probable of being malignant when locations of predictive probability (malignant scores) form of a cluster with at least twice variation size.

48. The apparatus or method of any preceding or following embodiment, wherein the predictive probability is represented as: Predictive Probability (malignant scores)=P (cancerous cell|genetic radiomic pathologic markers).

49. The apparatus or method of any preceding or following embodiment, wherein the predictive probability is represented as: Predictive Probability (malignant scores)=P (cancerous cell at local clinic level)*likelihood(cancerous cell, genetic radiomic pathologic markers).

As used herein, the singular terms "a," "an," and "the" may include plural referents unless the context clearly dictates otherwise. Reference to an object in the singular is not intended to mean "one and only one" unless explicitly so stated, but rather "one or more."

As used herein, the term "set" refers to a collection of one or more objects. Thus, for example, a set of objects can include a single object or multiple objects.

As used herein, the terms "substantially" and "about" are used to describe and account for small variations. When used in conjunction with an event or circumstance, the terms can refer to instances in which the event or circumstance occurs precisely as well as instances in which the event or circumstance occurs to a close approximation. When used in conjunction with a numerical value, the terms can refer to a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, "substantially" aligned can refer to a range of angular variation of less than or equal to ±10°, such as less than or equal to ±5°, less than or equal to ±4°, less than or equal to ±3°, less than or equal to ±2°, less than or equal to ±1°, less than or equal to ±0.5°, less than or equal to ±0.1°, or less than or equal to ±0.05°.

Additionally, amounts, ratios, and other numerical values may sometimes be presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

All structural and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

TABLE 1

Determining Predictive Probability

```
Model {
# Prior & N observation
    for(i in 1:N) {
        PCC[i] ~ dbern(p[i])
        logit(p[i])< -b0 + b1*Markerl[i] + b2*Marker2[i]
            +b3*Marker3[i] + u[group[i]]
    }
# M groups
    for(j in 1:M) {
        u[j] ~ dnorm(o, tau)
    }
# Priors
    b0 ~ dnorm(0, 1.0E-12)
    b1 ~ dnorm(0, 1.0E-12)
    b2 ~ dnorm(0, 1.0E-12)
    b3 ~ dnorm(0, 1.0E-12)
#Hyperprior
    tau ~ dgamma(0.001, 0.001)
# Positive predicted value
    where Marker1=10, Marker2=20, and Marker3=30
    PPOS < -1/(1+exp(-(b0 + b1*10 + b2*20 + b3*30)))
# data
# Initialization
    list(b0=0.1, b1=0.1, b2=0.1, b3=0.1)
```

TABLE 2

Prostate Registration Pipeline

```
<library imports>
AFFINE_CONF = <file path to Affine Elastix configuration>
```

TABLE 2-continued

Prostate Registration Pipeline

```
NONRIGID_CONF = <file path to non-rigid B-Spline Elastix
    configuration>
class TemplateStruct:
    def __init__ (self, img, mask, dt, comb):
        self.img = img
        self.mask = mask
        self.dt = dt
        self.comb = comb
class ProstateTemplateRegistration:
# Constructor to specify source directory of moving images,
# destination directory to store transformed images, and
# the fixed image template
def __init__ (self, source_dirs, dest_dir, template=None):
    self._list_of_proc_dirs = source_dirs
    self._dest_dir = dest_dir
    self._template = template
# If a template is not specified when initializing prostate
# registration, then specify one with this method
def set_template(self,img_path,mask_path,dt_path,comb_path):
    self._template = TemplateStruct(img_path,mask_path,
        dt_path, comb_path)
# First step in prostate registration - Affine registration
# of moving image and corresponding distance transform
# to fixed template
def register_multi_affine(self):
    for proc_dir_path in self._list_of_proc_dirs:
        <Multi-affine registration of moving image and moving
        image distance transform to fixed template using elastix>
# Prior to B-spline deformation (step 2 of prostate registration),
# the Affine transformed moving image is multiplied with its
# prostate mask to suppress other anatomy
def setup_register_bspline(self):
    for proc_dir_path in self._list_of_proc_dirs:
        <multiply affine transformed moving image with affine
        transformed prostate mask>
# Second step in prostate registration, B-spline deformation of
# moving image prostate to template prostate, note that anatomy
# outside the prostate is suppressed prior to this step
def register_bspline(self):
    for proc_dir_path in self._list_of_proc_dirs:
        <B-spline deform moving image prostate to fixed template
        prostate>
# Transform all moving images - source image, prostate contour and
# tumor target # contours using the deformation field created
# through registration
def transform(self):
    for proc_dir_path in self._list_of_proc_dirs:
        moving_list = <compile list of images to transform - moving
        image (grayscale), prostate and tumor contours (black &
        white)>
        # Transform prostate mask and lesion data
        for file in moving_bw_list:
            <Transform moving image to fixed template space>
# Post-processing step after transformation, make sure prostate
# and tumor masks are binary; and that tumor masks are trimmed if
# they exceed the prostate boundary
def transform_postprocess(self):
    proc_file_path = getTemporaryFile( )
    for proc_dir_path in self._list_of_proc_dirs:
        <Binarize the prostate and all tumor target masks with a
        threshold of 0.5>
        <Multiply all tumor target masks with the prostate mask>
def __main__( ):
    source_dir = <source directory containing raw contour and
        moving image data>
    destination_dir1 = <intermediate destination directory to store
        transformed contour and moving image data>
    destination_dir2 = <final destination directory to store
        transformed contour and moving image data>
    template_obj = TemplateStruct(<specify fixed template
        parameters>)
# Step 1: Multi-Affine Registration
proc_regis_wrap1 = ProstateTemplateRegistration(source_dir,
    destination_dir1, template=template_obj)
proc_regis_wrap1.register_multi_affine( )
proc_regis_wrap1.transform( )
proc_regis_wrap1.transform_postprocess( )
# Step 2: B-Spline Registration
proc_regis_wrap2 = ProstateTemplateRegistration(destination_dir1,
    destination_dir2, template=template_obj)
proc_regis_wrap2.setup_register_bspline( )
proc_regis_wrap2.register_bspline( )
proc_regis_wrap2.transform( )
proc_regis_wrap2.transform_postprocess( )
if __name__ == "__main__":
    __main__( )
#                      Population Map Building
<library imports>
class BuildPopulationMap:
# Contructor, specify input directory with transformed prostate
and tumor
# contours
def __init__ (self, source_dir):
    self._list_of_proc_dirs = [ ]
    for dirc in os.listdir(source_dir):
        if os.path.isdir(os.path.join(source_dir, dirc)):
            self._list_of_proc_dirs.append(os.path.join(source_dir, dirc))
    self.combine_list = [ ]
# Method to create a filtered list of contours to include in the
population map,
# can be used to build population map specific to tumor type
def generate_filtered_list(self, filter_str):
    self.combine_list = [ ]
    for dir_path in self._list_of_proc_dirs:
        found_files = glob.glob(os.path.join(dir_path, filter_str))
        for found_file in found_files:
            self.combine_list.append(found_file)
# Method to combine specific contours into a population map
def combine(self, result_file_path):
    shutil.copy(self.combine_list[0], result_file_path)
    if len(self.combine_list) > 1:
        for combine_file in self.combine_list:
            <Add all tumor contours together>
            <Divide by the total number of tumor contours to get probability>
def __main__( ):
    src_dir = <Specify source directory of all transformed tumor
        contours>
    proc_pmap = BuildPopulationMap(src_dir)
    # Include only contours of index lesions for example
    proc_pmap.generate_filtered_list ("*Lesion Index*")
    proc_pmap.combine(os.path.join(src_dir, "result_index_lesions"))
if __name__ == "__main__":
    __main__( )
```

What is claimed is:

1. An apparatus for generating a probability map of a tumor location on diagnostic medical imaging of a prostate, the apparatus comprising:
   (a) a processor; and
   (b) a non-transitory computer-readable memory storing instructions executable by the processor;
   (c) wherein said instructions, when executed by the processor, perform steps comprising:
      (i) acquiring diagnostic medical imaging and metadata from medical imaging of a prostate;
      (ii) obtaining prostate information from a clinical database;
      (iii) constructing an enriched prostate template from a subset of high resolution and segmented candidate prostates from the clinical database;
      (iv) generating a registration framework based on the enriched prostate template;
      (v) registering each diagnostic medical imaging image with the registration framework;
      (vi) creating a probability map of tumor location; and
      (vii) transforming the registered diagnostic medical images and probability map into an output image incorporating the probability map on each registered diagnostic medical image.

2. The apparatus recited in claim 1, wherein said instructions when executed by the processor performs registering the diagnostic medical imaging comprising registering the prostate across multiple subjects to the space of a common template.

3. The apparatus recited in claim 1, wherein said diagnostic medical imaging comprises T2-weighted magnetic resonance (MR) images.

4. The apparatus recited in claim 1, wherein said instructions when executed by the processor generates the enriched prostate template comprising:
 (a) an intensity-based affine prostate template;
 (b) an intensity-based non-rigid prostate template;
 (c) a binary segmentation of the non-rigid prostate template; and
 (d) a cascading registration pipeline involving affine registration followed by a non-rigid B-spline registration of candidate prostate images to the enriched template.

5. The apparatus recited in claim 1, wherein said instructions when executed by the processor performs registering the diagnostic medical imaging which further comprises: (a) utilizing a randomly chosen candidate from the subset of candidate prostates as an initial template; and (b) registering other candidate prostates through a cascaded application of affine and non-rigid B-spline transformations.

6. The apparatus recited in claim 1, wherein said instructions when executed by the processor perform said registering the diagnostic medical imaging which further comprises: (a) computing an average deformation field; and (b) applying the average deformation field to all candidates in the subset of candidate prostates.

7. The apparatus recited in claim 1, wherein said instructions when executed by the processor performs said registering the diagnostic medical imaging which further comprises deriving a final enriched prostate template from median intensities of the subset of candidate prostates.

8. The apparatus recited in claim 1, wherein said instructions when executed by the processor perform said registering the diagnostic medical imaging which further comprises identifying an enriched prostate template mask as regions where at least 50% of deformed candidate prostate segmentations overlap.

9. The apparatus recited in claim 1, wherein said instructions when executed by the processor perform registering of the diagnostic medical imaging which further comprises (a) creating a prostate template, and (b) affinely registering the candidate prostate and its corresponding segmentation to the prostate template and its prostate segmentation.

10. The apparatus recited in claim 1, wherein said instructions when executed by the processor perform said registering the diagnostic medical imaging which further comprises initializing the registration process with alignment of centroids of the prostate segmentation in the candidate and template to improve performance of the affine registration step.

11. The apparatus recited in claim 1, wherein said instructions when executed by the processor perform said registering the diagnostic medical imaging which further comprises obtaining a final affine transformation by performing multi-resolution registration over four resolutions through a smoothing image pyramid.

12. The apparatus recited in claim 1, wherein said registering the diagnostic medical imaging further comprises using a multi-metric cost function for the registration, with the cost function comprising (a) image intensity based mutual information (MI) between the T2 image and the affine template image; and (b) sum of square difference (SSD) between the distance transform of the subject object segmentation and the template prostate mask.

13. The apparatus recited in claim 1, wherein said instructions when executed by the processor perform said registering the diagnostic medical imaging which further comprises performing a non-rigid B-spline registration in which a candidate object is deformed to the same shape as prostate template.

14. The apparatus recited in claim 1, wherein said instructions when executed by the processor perform said registering the diagnostic medical imaging which further comprises: (a) performing multi-resolution registration over four resolutions through a smoothing image pyramid to register a subject diagnostic medical imaging to a prostate template, and (b) utilizing intensity-based mutual information of the mask images is as a cost function.

15. The apparatus recited in claim 1, wherein said instructions when executed by the processor perform said registering the diagnostic medical imaging which further comprises registering each available candidate object to a prostate template using an enriched prostate template model and inter-subject object registration.

16. The apparatus recited in claim 1, wherein said instructions when executed by the processor perform said registering the diagnostic medical imaging which further comprises deforming volumetric contours of tumors, including both true and false positives with respect to pathology, utilizing corresponding transformations computed from registering the diagnostic medical imaging.

17. The apparatus recited in claim 1, wherein said instructions when executed by the processor perform said registering the diagnostic medical imaging which further comprises building a final probabilistic model from a sum of all deformed tumor contours divided by a total number of prostate subjects.

18. The apparatus recited in claim 1, wherein said instructions when executed by the processor perform said creating a probability map of tumor location further comprises designating a location in the diagnostic medical imaging as probable of being malignant when locations of predictive probability, including malignant scores, form a cluster as an estimate.

19. The apparatus recited in claim 18, wherein the predictive probability of malignant scores is determined by the probability of cancerous cell of a tumor location given genetic, radiologic, and pathologic markers from a subject or a tumor lesion.

20. The apparatus recited in claim 18, wherein the predictive posterior probability of malignant scores is determined by the product of two parts: (a) a prior knowledge of a prevalence of a specific type of cancer at local clinical level; and (b) a likelihood function of the joint distribution of the location of cancerous cell of tumor, genetic, radiomic, and pathologic markers from subject or a tumor lesion.

21. The apparatus recited in claim 1, wherein said instructions when executed by the processor perform said creating a probability map of tumor location further comprises designating a location in the diagnostic medical imaging as probable of being malignant when locations of predictive probability, including malignant scores, form a cluster as well as provide a confidence bound around a tumor.

22. The apparatus recited in claim 21, wherein a confidence interval of predictive posterior probability of malignant scores is determined by the probability of cancerous cells of a tumor given occurrence of genetic, radiomic, and pathologic markers from a subject or a tumor lesion.

23. The apparatus recited in claim 21, wherein said confidence interval of predictive posterior probability, including malignant scores, is determined by the product of two parts: (a) the prior knowledge of a prevalence of a specific type of cancer at a local clinical level; and (b) the likelihood function of a joint distribution of cancerous cell of tumor, genetic, radiomic, and pathologic markers from a subject or a tumor lesion.

24. A method of generating a probability map of a tumor location on diagnostic medical imaging of a prostate, comprising:
- (a) acquiring diagnostic medical imaging and metadata from medical image scanning of a prostate;
- (b) obtaining prostate information from a clinical database;
- (c) constructing an enriched prostate template from a subset of high resolution and segmented candidate prostates from the clinical database;
- (d) generating a registration framework based on the enriched prostate template;
- (e) registering each diagnostic medical imaging image with the registration framework;
- (f) creating a probability map of tumor location; and
- (g) transforming the registered diagnostic medical images and probability map into an output image incorporating the probability map on each registered diagnostic medical image.

* * * * *